(12) United States Patent
Lee et al.

(10) Patent No.: US 7,540,647 B2
(45) Date of Patent: Jun. 2, 2009

(54) MEDICAL INSPECTION DEVICES

(75) Inventors: Kun-Feng Lee, Kaohsiung County
(TW); Ching-Yi Wu, Taoyuan County
(TW); Yu-Shih Chen, Taoyuan County
(TW); Yuh-Jiuan Lin, Taipei County
(TW); Hsi Feng Kao, Taipei County
(TW)

(73) Assignee: Industrial Technology Research Institute, Hsinchu (TW)

( * ) Notice: Subject to any disclaimer, the term of this patent is extended or adjusted under 35 U.S.C. 154(b) by 77 days.

(21) Appl. No.: 11/688,776

(22) Filed: Mar. 20, 2007

(65) Prior Publication Data
US 2007/0225557 A1   Sep. 27, 2007

(30) Foreign Application Priority Data
Mar. 22, 2006   (TW) .............................. 95109857 A

(51) Int. Cl.
*A61B 1/24*   (2006.01)
*H04N 7/18*   (2006.01)
*A61B 1/06*   (2006.01)

(52) U.S. Cl. ........................ 362/573; 362/572; 362/138; 362/140; 348/66; 348/68; 433/29; 433/30; 600/109; 600/129; 600/160; 600/175

(58) Field of Classification Search ................ 362/109, 362/119, 362, 800, 418, 138, 140, 572, 573, 362/804; 433/29, 30; 600/101, 109, 129, 600/160, 175; 8/109, 119, 362, 800, 418; 348/66, 68, 222.1
See application file for complete search history.

(56) References Cited

U.S. PATENT DOCUMENTS

| 3,884,222 | A |   | 5/1975 | Moore |
| 4,993,945 | A | * | 2/1991 | Kimmelman et al. ......... 433/30 |
| 5,181,848 | A | * | 1/1993 | Griffith ........................ 433/30 |
| 5,429,502 | A |   | 7/1995 | Cooper et al. |
| 5,741,132 | A | * | 4/1998 | Usui et al. ..................... 433/30 |
| 5,908,294 | A |   | 6/1999 | Schick et al. |
| 6,002,424 | A | * | 12/1999 | Rapa et al. .................... 348/66 |
| 6,050,939 | A |   | 4/2000 | Pak Wai |
| 6,217,512 | B1| * | 4/2001 | Salo et al. ................... 600/160 |
| 6,276,934 | B1|   | 8/2001 | Rakocz |
| 6,626,825 | B2|   | 9/2003 | Tsai |
| 6,908,307 | B2| * | 6/2005 | Schick ........................ 433/29 |
| 6,958,766 | B2| * | 10/2005 | Cooper ........................ 348/66 |
| 7,021,798 | B2| * | 4/2006 | Tsimerman et al. ......... 362/362 |

* cited by examiner

*Primary Examiner*—Jacob Y Choi
(74) *Attorney, Agent, or Firm*—Quintero Law Office

(57) ABSTRACT

A medical inspection device. A housing includes a transparent plate. A circuit board is disposed in the housing. At least one light-emitting element is disposed on and electrically connected to the circuit board. The light-emitting element is opposite to the transparent plate. Light from the light-emitting element is output to the exterior of the housing through the transparent plate. An image sensor is disposed on and electrically connected to the circuit board. The image sensor is opposite to the transparent plate. An image in the exterior of the housing is received by the image sensor through the transparent plate and converted into an image signal thereby. A grip is detachably connected to the housing. A signal transmission line is detachably connected to the circuit board and fit in the grip and extends to the exterior of the grip, outputting the image signal.

7 Claims, 4 Drawing Sheets

MEDICAL INSPECTION DEVICES

BACKGROUND OF THE INVENTION

1. Field of the Invention

The invention relates to medical inspection, and in particular to medical inspection devices providing convenient operation and digital function for medical inspection.

2. Description of the Related Art

FIG. 1 is a schematic perspective view of a conventional laryngoscope 1. Conventionally, an operator (or a doctor) puts the laryngoscope 1 into a mouth cavity of a subject (or a patient) and inspects targets therein by reflection of a reflective mirror 11 thereof. Then, the operator (doctor) visually examines images on the reflective mirror 11, thereby judging the condition of the targets. The inspected targets are generally located in nasopharynx and larynx of the subject. Nevertheless, there are some drawbacks during inspection of the mouth cavity of the subject using the laryngoscope 1. For example, illumination in the mouth cavity is often insufficient, such that clear images cannot be obtained. Moreover, interaction between the operator (doctor) and the subject (patient) and narration from the operator (doctor) are not practical.

U.S. Pat. No. 6,050,939 discloses a laryngoscope with a palm-grippable housing. Two torches are fixed to the palm-grippable housing, providing upward and downward illumination for a throat mirror.

U.S. Pat. No. 3,884,222 discloses a laryngoscope obtaining images with optical fiber connected to the back of a conventional throat mirror.

Although a (soft) fiber laparoscope or an (hard) anesthetization laryngoscope can be used to inspect the nasopharynx, larynx, mouth cavity, or nasal cavity of the subject, anesthetization must be utilized therewith, discomforting the subject. Additionally, requirement for high maintenance costs dictates limited applicability of the (soft) fiber laparoscope or (hard) anesthetization laryngoscope in most clinical environments.

Moreover, U.S. Pat. No. 5,429,502 discloses an electronic video dental camera providing illumination via optical fiber and receiving images using an image sensor.

U.S. Pat. No. 5,908,294 and U.S. Pat. No. 6,276,934 disclose handheld dental video cameras transmitting received external light via optical paths to rear image sensors.

U.S. Pat. No. 6,626,825 discloses a medical inspection device, for inspection of an ear passage, guiding light from an LED via optical fiber to an exit thereof, providing illumination. The medical inspection device comprises an image sensor capturing images and transmitting the same to an LCD panel on the back of the medical inspection device. The LCD panel displays the images.

Hence, there is a need for medical inspection devices providing a diagnostician with convenient operation.

BRIEF SUMMARY OF THE INVENTION

A detailed description is given in the following embodiments with reference to the accompanying drawings.

An exemplary embodiment of the invention provides a medical inspection device for inspection of a nasopharynx, a larynx, a mouth cavity, a nasal cavity, an ear passage, skin, etc, comprising a housing, a circuit board, at least one light-emitting element, an image sensor, a grip, and a signal transmission line. The housing comprises a transparent plate. The circuit board is disposed in the housing. The light-emitting element is disposed on and electrically connected to the circuit board. The light-emitting element is opposite to the transparent plate. Light from the light-emitting element is output to the exterior of the housing through the transparent plate. The image sensor is disposed on and electrically connected to the circuit board. The image sensor is opposite to the transparent plate. An image in the exterior of the housing is received by the image sensor through the transparent plate and converted into an image signal thereby. The grip is detachably connected to the housing. The signal transmission line is detachably connected to the circuit board and fit in the grip and extends to the exterior of the grip, outputting the image signal.

The medical inspection device further comprises a reflective mirror disposed in the housing and comprising a reflective surface attached to the transparent plate.

The medical inspection device further comprises a heater connected to the reflective mirror and electrically connected to the circuit board.

The heater comprises a heating coil or resistor.

The medical inspection device further comprises a power line detachably connected to the circuit board, fit in the grip, and extending to the exterior of the grip.

The medical inspection device further comprises a rechargeable module detachably connected to the grip and electrically connected to the circuit board via the grip.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

First Embodiment

Figure 1:
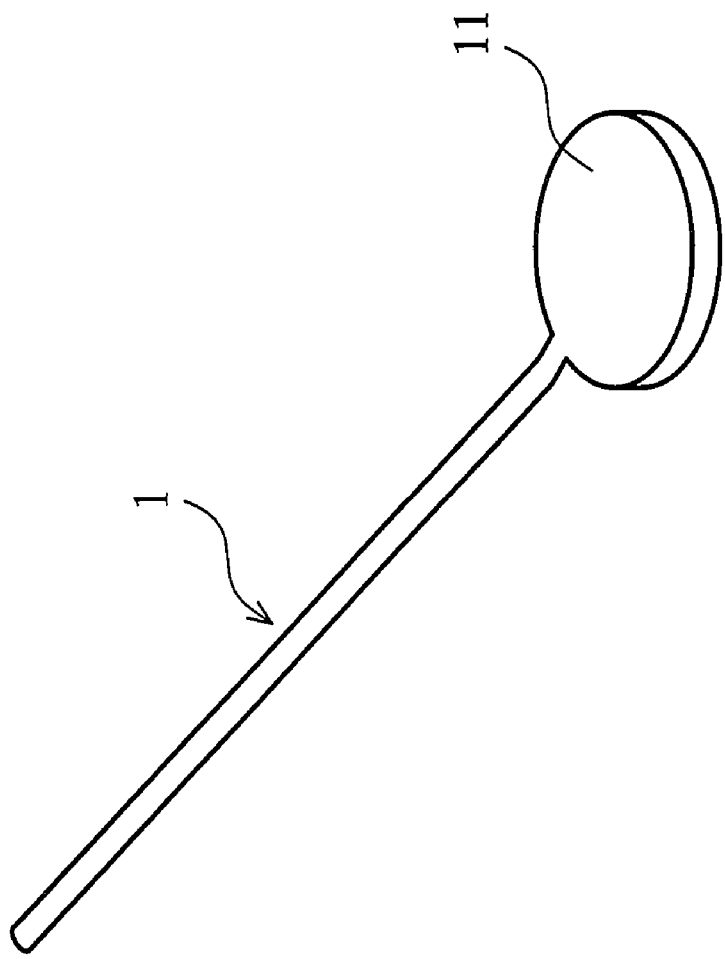
FIG. 1 is a schematic perspective view of a conventional laryngoscope.
Figure 2A:
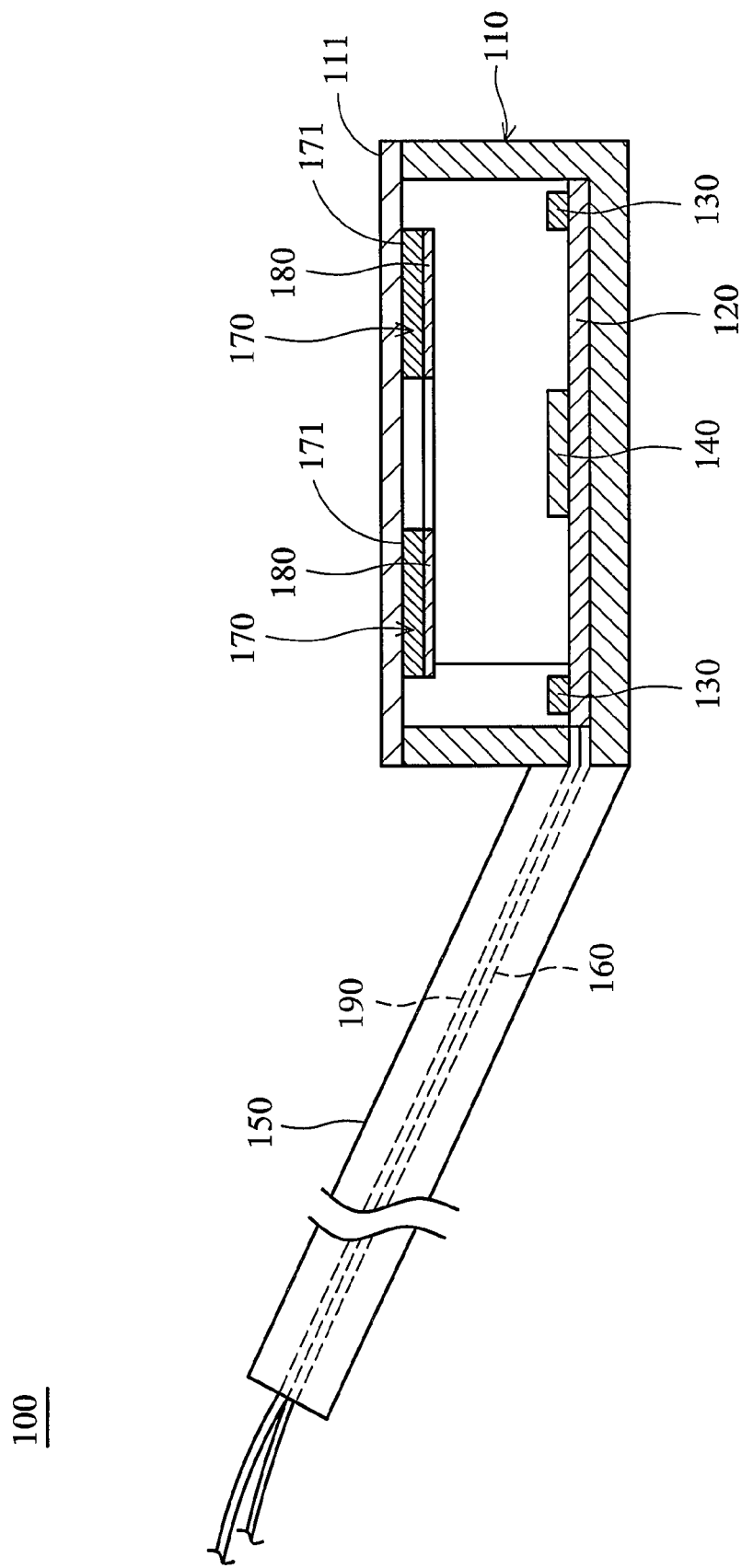
FIG. 2A is a partial cross section and side view of a medical inspection device of a first embodiment of the invention.
Figure 2B:
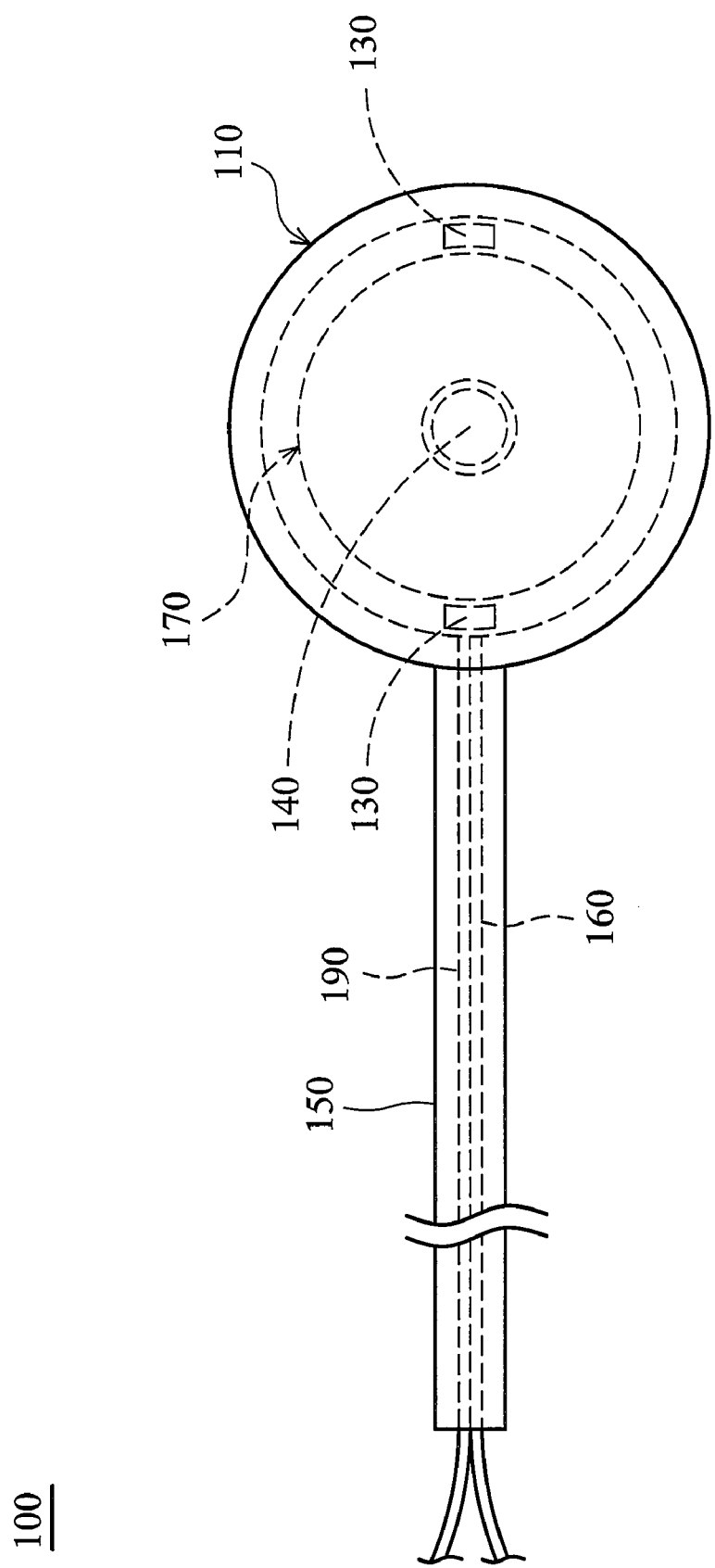
FIG. 2B is a schematic top view of the medical inspection device of the embodiment of the invention.

Referring to FIG. 2A and FIG. 2B, a medical inspection device 100 comprises a housing 110, a circuit board 120, multiple light-emitting elements 130, an image sensor 140, a grip 150, a signal transmission line 160, a reflective mirror 170, a heater 180, and a power line 190.

The housing 110 comprises a transparent plate 111.

The circuit board 120 is disposed in the housing 110.

The light-emitting elements 130 are disposed on and electrically connected to the circuit board 120. Specifically, the light-emitting elements 130 oppose the transparent plate 111 of the housing 110. Additionally, the light-emitting elements 130 may be LEDs.

The image sensor 140 is disposed on and electrically connected to the circuit board 120. Similarly, the image sensor 140 is opposite to the transparent plate 111 of the housing 110. Additionally, the image sensor 140 may be a CCD or a CMOS.

The grip 150 is detachably connected to the housing 110. Specifically, after separation from the housing 110, the grip 150 can be sterilized or replaced.

The signal transmission line 160 is detachably connected to the circuit board 120 and fit in the grip 150. Additionally, the signal transmission line 160 extends to the exterior of the grip 150, connecting to a computer (not shown) or a monitor (not shown).

The reflective mirror 170 is disposed in the housing 110 and comprises a reflective surface 171. Specifically, the reflective surface 171 is attached to the transparent plate 111 and faces the exterior of the housing 110. Accordingly, an operator can easily locate a target being inspected by the naked eye, especially for inspection of a nasopharynx or larynx.

The heater 180 is connected to the reflective mirror 170 and electrically connected to the circuit board 120. Here, the heater 180 heats the transparent plate 111 connected to the reflective mirror 170, removing mist therefrom. Moreover, the heater 180 may be a heating coil or resistor.

The power line 190 is detachably connected to the circuit board 120 and fit in the grip 150. Additionally, the power line 190 extends to the exterior of the grip 150, transporting power to the circuit board 120.

When an operator inspects the nasopharynx, larynx, mouth cavity, nasal cavity, or ear passage of a subject using the medical inspection device 100, light from the light-emitting elements 130 is output to the exterior of the housing 110 through the transparent plate 111 thereof, illuminating the same. The operator can initially locate a target by watching the reflective mirror 170 of the medical inspection device 100. When the target is found, an image thereof is received by the image sensor 140 through the transparent plate 111 and converted into an image signal thereby. The image signal is transmitted to the computer via the signal transmission line 160. The monitor then displays the magnified image of the target. At this point, the operator can easily inspect the magnified target on the monitor and the subject may thereby understand the inspection or even communicate with the operator.

Second Embodiment

Elements corresponding to those in the first embodiment share the same reference numerals.

Figure 3:
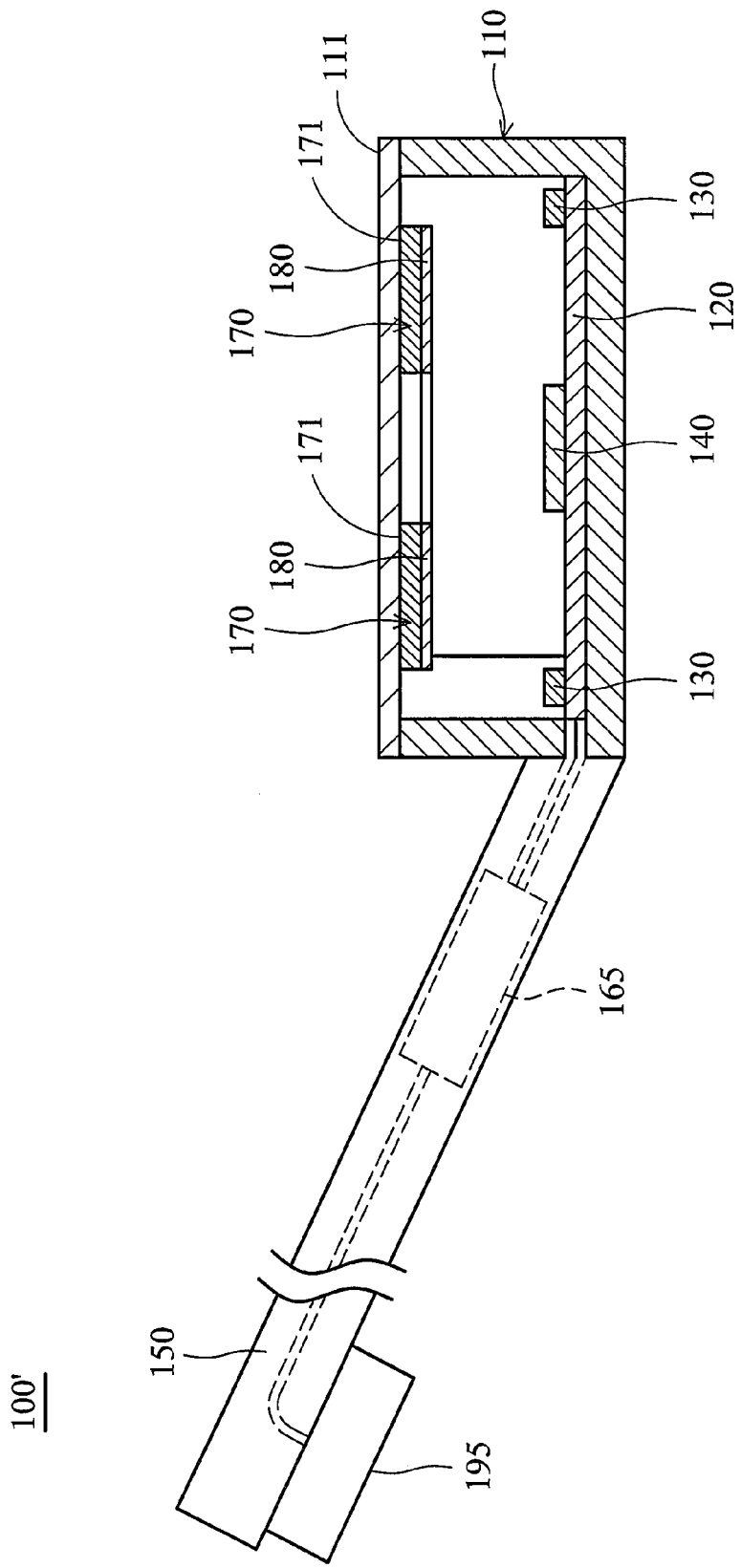
FIG. 3 is a partial cross section and side view of a medical inspection device of a second embodiment of the invention.

Referring to FIG. 3, a medical inspection device 100' comprises a housing 110, a circuit board 120, multiple light-emitting elements 130, an image sensor 140, a grip 150, a wireless transmission module 165, a reflective mirror 170, a heater 180, and a rechargeable module 195.

As shown in FIG. 3, the wireless transmission module 165 is detachably disposed in the grip 150 and electrically connected to the circuit board 120 via the (interior of the) grip 150.

The rechargeable module 195 is detachably connected to the grip 150 and electrically connected to the circuit board 120 and wireless transmission module 165 via the (interior of the) grip 150. Specifically, the rechargeable module 195 comprises a rechargeable battery (not shown) supplying power to the circuit board 120 and wireless transmission module 165.

Accordingly, as the medical inspection device 100' provides the wireless transmission module 165 and rechargeable module 195, signal transmission and power lines can be omitted, thus enhancing convenience of operation.

Structure, disposition, and function of other elements in this embodiment are the same as those in the first embodiment, and explanation thereof is omitted for simplicity.

When an operator inspects the nasopharynx, larynx, mouth cavity, nasal cavity, or ear passage of a subject using the medical inspection device 100', light from the light-emitting elements 130 is output to the exterior of the housing 110 through the transparent plate 111 thereof, illuminating the same. The operator can initially locate a target by watching the reflective mirror 170 of the medical inspection device 100'. When the target is found, an image thereof is received by the image sensor 140 through the transparent plate 111 and converted into an image signal thereby. The image signal is transmitted to a computer by the wireless transmission module 165. A monitor connected to the computer then displays the magnified image of the target. At this point, the operator can easily inspect the magnified target on the monitor and the subject may thereby understand the inspection or even communicate with the operator.

In conclusion, as the light-emitting elements and image sensor are disposed on the same circuit board, the size of the housing is reduced. Thus, the overall size of the disclosed medical inspection devices is reduced.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A medical inspection device, comprising:
   a housing comprising a transparent plate;
   a reflective mirror disposed in the housing and comprising a reflective surface formed onto the transparent plate, the reflective surface facing the exterior of the housing;
   a circuit board disposed in the housing;
   at least one light-emitting disposed on and electrically connected to the circuit board, wherein the light-emitting element is opposite to the transparent plate, and light from the light-emitting element is output to the exterior of the housing through the transparent plate;
   an image sensor disposed on and electrically connected to the circuit board, wherein the image sensor is opposite to the transparent plate, and an image in the exterior of the housing is received by the image sensor through the transparent plate and converted into an image signal thereby;
   a grip connected to the housing; and
   a signal transmission line connected to the circuit board, fit in the grip, and extending to the exterior of the grip, outputting the image signal.

2. The medical inspection device as claimed in claim 1, further comprising a heater connected to the reflective mirror and electrically connected to the circuit board.

3. The medical inspection device as claimed in claim 1, further comprising a power line connected to the circuit board, fit in the grip, and extending to the exterior of the grip.

4. The medical inspection device as claimed in claim 1, further comprising a rechargeable module connected to the grip and electrically connected to the circuit board via the grip.

5. A medical inspection device, comprising:

a housing comprising a transparent plate;

a reflective mirror disposed in the housing and comprising a reflective formed surface onto the transparent plate, the reflective surface facing the exterior of the housing;

a circuit board disposed in the housing;

at least one light-emitting element disposed on and electrically connected to the circuit board, wherein the light-emitting element is opposite to the transparent plate, and light from the light-emitting element is output to the exterior of the housing through the transparent plate;

an image sensor disposed on and electrically connected to the circuit board, wherein the image sensor is opposite to the transparent plate, and an image in the exterior of the housing is received by the image sensor through the transparent plate and converted into an image signal thereby;

a grip connected to the housing; and a wireless transmission module disposed in the grip and electrically connected to the circuit board via the grip.

6. The medical inspection device as claimed in claim 5, further comprising a heater connected to the reflective mirror and electrically connected to the circuit board.

7. The medical inspection device as claimed in claim 5, further comprising a rechargeable module connected to the grip and electrically connected to the circuit board and wireless transmission module via the grip.

* * * * *